(12) United States Patent
Singer

(10) Patent No.: US 7,003,346 B2
(45) Date of Patent: Feb. 21, 2006

(54) METHOD FOR ILLNESS AND DISEASE DETERMINATION AND MANAGEMENT

(76) Inventor: Michaeal G. Singer, P.O. Box 244, 705 S. Lake Huron Shore Rd., Harrisville, MI (US) 48740

( * ) Notice: Subject to any disclaimer, the term of this patent is extended or adjusted under 35 U.S.C. 154(b) by 21 days.

(21) Appl. No.: 10/701,004

(22) Filed: Nov. 4, 2003

(65) Prior Publication Data

US 2004/0092841 A1    May 13, 2004

Related U.S. Application Data

(63) Continuation-in-part of application No. 09/848,242, filed on May 3, 2001, now Pat. No. 6,587,715.

(60) Provisional application No. 60/424,828, filed on Nov. 8, 2002.

(51) Int. Cl.
*A61B 5/05* (2006.01)

(52) U.S. Cl. .................. 600/547; 600/386; 128/898
(58) Field of Classification Search ............... 600/300, 600/384–386, 506, 546–547, 536, 587; 128/898; 439/586; 324/713, 600
See application file for complete search history.

(56) References Cited

U.S. PATENT DOCUMENTS

| | | | | |
|---|---|---|---|---|
| 3,971,366 A | * | 7/1976 | Motoyama | 600/384 |
| 4,008,712 A | * | 2/1977 | Nyboer | 600/547 |
| 4,880,014 A | * | 11/1989 | Zarowitz et al. | 600/547 |
| 4,911,175 A | * | 3/1990 | Shizgal | 600/547 |
| 5,615,689 A | | 4/1997 | Kotler | |
| 6,236,886 B1 | | 5/2001 | Cherepenin et al. | |
| 6,631,292 B1 | * | 10/2003 | Liedtke | 600/547 |
| 2001/0023362 A1 | | 9/2001 | Kubayashi | |
| 2002/0123694 A1 | * | 9/2002 | Organ et al. | 600/547 |

* cited by examiner

*Primary Examiner*—Tu Hoang
(74) *Attorney, Agent, or Firm*—Irving M. Weiner; Pamela S. Burt; Weiner & Burt, P.C.

(57) ABSTRACT

A method for detecting the presence and severity of illness, the effectiveness of treatment interventions, and the ability to change treatment to be more effective or aggressive, to optimize outcomes, to limit morbidity and mortality, and to illustrate a patient's prognosis, including the steps of using whole body impedance analysis to measure a patient's resistance, reactance, phase angle, and related electrical values at a healthy baseline, and thereafter in relation to the patient's complaints, evaluating temporal or progressive nature of negative values or diminution of the measured values of resistance, reactance, phase angle, and related electrical values over time.

20 Claims, 1 Drawing Sheet

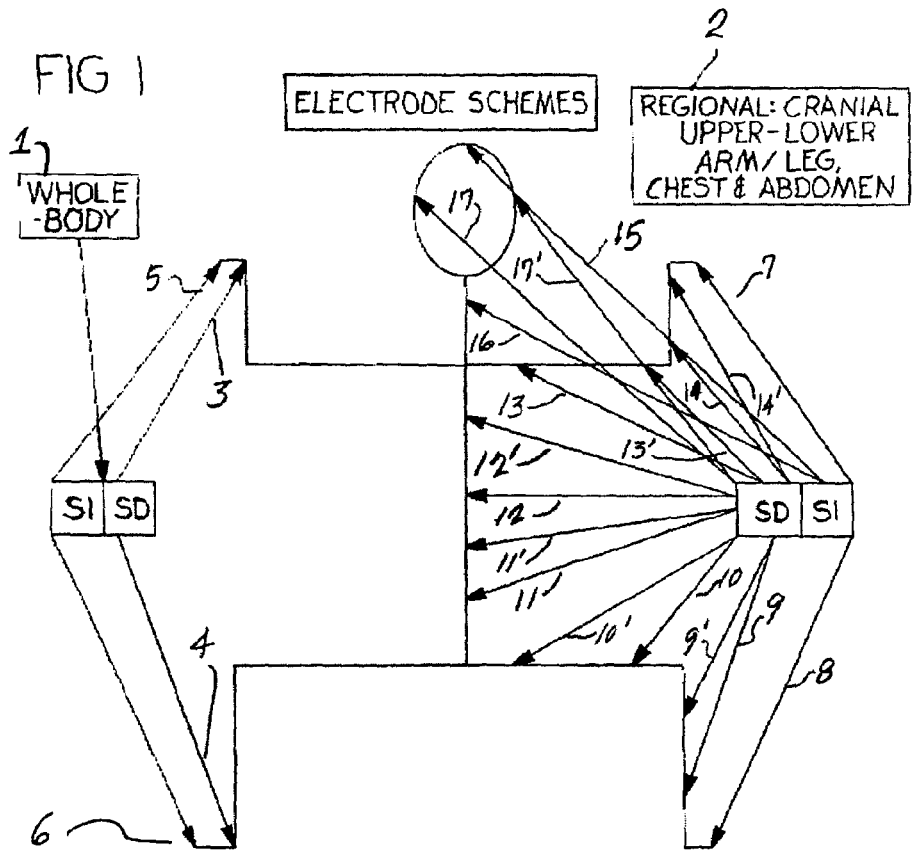
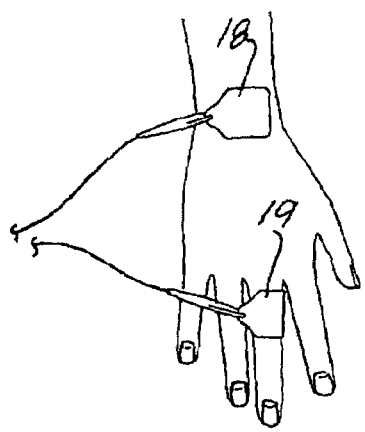
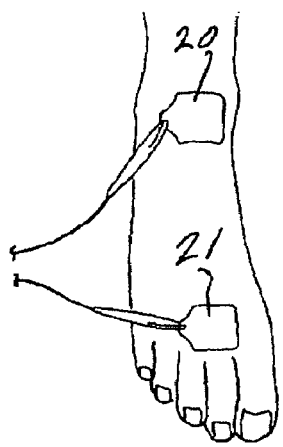
FIG 1
FIG 2
FIG 3

METHOD FOR ILLNESS AND DISEASE DETERMINATION AND MANAGEMENT

The present application is based on and claims priority from U.S. Provisional Patent Application Ser. No. 60/424,828 filed Nov. 8, 2002, which is a continuation-in-part of U.S. patent application Ser. No. 09/848,242 filed May 3, 2001 now U.S. Pat. No. 6,587,715. The complete disclosure of both said prior applications are incorporated herein by reference thereto.

The present invention relates generally to a method and apparatus for use in detecting the presence and severity of illness, the effectiveness of treatment interventions, and the ability to change treatment to be more effective or aggressive; to optimize outcome, limit morbidity and mortality and illustrate the patent's prognosis.

More particularly, the present invention relates to the method and apparatus mentioned above which incorporates the utilization of bioelectrical impedance analysis (BIA) in a biological model for body composition analysis (BCA) to provide an objective assessment of an organ's and/or biological entity's volume and distribution of fluids and tissue as well as the electrical health of cells and membranes.

Another aspect of the present invention relates to a method for determining illness of a biological entity, progression to death of said biological entity, and/or timing of death of said biological entity, and also relates to a method of organ vitality assessment for transplantation of said organ being assessed.

The terms "biological entity", "patient" and "subject" as used herein mean: "any and all human beings, animals and/or living organisms."

The term "non-acute death" as used herein means: "any death that does not occur acutely; it occurs more than four days (96 hours) from a precipitous event or illness; it is the end-point of a process whose duration exceeds the four-day reference; unlike that death resulting from a proximate, immediate or acute event, a 'non-acute death' occurs over time."

BACKGROUND OF THE INVENTION

The prior, but not necessarily relevant, art is exemplified by:

Bagno U.S. Pat. No. 2,111,135; Hanson U.S. Pat. No. 2,852,739; Tolles U.S. Pat. No. 3,085,566; Thomasset U.S. Pat. No. 3,316,896; Max et al. U.S. Pat. No. 3,498,288; Sigworth U.S. Pat. No. 3,882,851; Ghislaine et al. U.S. Pat. No. 4,823,804; Gallup et al. U.S. Pat. No. 5,372,141; Kotler U.S. Pat. No. 5,615,689; Brasile U.S. Pat. No. 6,024,698; Cherepenin et al. U.S. Pat. No. 6,236,866; and Kobayashi U.S. Patent Application Publication 2001/0023362.

The desiderata of the present invention are to avoid the animadversions of conventional methods and techniques, and to provide a novel method and apparatus for use in detecting the presence and severity of illness, the effectiveness of treatment interventions and the ability to change treatment to be more effective or aggressive; to optimize outcome, limit morbidity and mortality and illustrate the patient's prognosis, and to provide a novel method for determining illness of a biological entity, progression to death of said biological entity, and/or timing of death of said biological entity, and to provide a novel method of organ vitality assessment for transplantation and/or xenotransplantation of said organ being assessed.

SUMMARY OF THE INVENTION

The present invention provides a unique and novel method and apparatus for use in detecting the presence and severity of illness, the effectiveness of treatment interventions and the ability to change treatment to be more effective or aggressive; to optimize outcome, limit morbidity and mortality and illustrate the patient's prognosis.

The present invention provides a method for detecting the presence and severity of illness, the effectiveness of treatment interventions, and the ability to change treatment to be more effective or aggressive, to optimize outcome, limit morbidity and mortality and illustrate the patent's prognosis, comprising the steps of: employing the use of whole body impedance analysis to measure a patient's resistance, reactance, phase angle and related electrical values at a healthy baseline; and thereafter in relation to the patient's complaints, evaluating the temporal or progressive nature of negative values or diminution of the measured values over time.

The present invention also provides a method for determining illness of a biological entity, progression to non-acute death of said biological entity, or timing of non-acute death of said biological entity, comprising the steps of: providing normal values of resistance, reactance, phase angle, extracellular water volume, intracellular water volume, and membrane status of the whole body of the biological entity; measuring initial values of resistance, phase angle, extracellular water volume, intracellular water volume, and membrane status of the whole body of the biological entity; taking whole body measurements of phase angle, extracellular water volume, intracellular water volume, and membrane status at predetermined intervals of time; recording said whole body measurements; comparing initial values of said whole body measurements to said normal values of said whole body measurements and to serially measured values of said whole body measurements; and determining from said comparison steps hallmarks of said illness of said biological entity, said progression to said non-acute death of said biological entity, or said timing of non-acute death of said biological entity.

The present invention further provides a method of organ vitality assessment for transplantation of said organ being assessed, comprising the steps of: placing signal introduction electrodes on opposite lateral peripheral borders of said organ upon harvesting of said organ; placing signal detection electrodes at superior and inferior borders of said organ for a first part of an initial measurement upon said harvesting of said organ; measuring and recording first values of resistance and reactance of said organ in said initial measurement; then placing said signal introduction electrodes on said superior and said inferior borders of said organ; placing said signal detection electrodes on said opposite lateral borders of said organ; measuring and recording second values of said resistance and said reactance of said organ; and comparing said first and second values to normal values to determine if said organ is acceptable or not for said transplantation.

It is a primary objective of the present invention to empower the health care provider and patient by detecting and characterizing the nature of illness and injury to include episodic, serious, and non-episodic illness and injury, its progression and the effectiveness of treatment interventions and the prognosis of the patient.

In conjunction with the foregoing, the present invention also provides a method for determining illness of a biological entity, progression to death of said biological entity, and/or timing of death of said biological entity, comprising the steps of: taking whole body measurements of resistance, reactance, phase angle, extracellular water volume, and intracellular water volume at predetermined intervals of time; recording said whole body measurements; comparing initial values of said whole body measurements to normal values of said whole body measurements and to serially measured values of said whole body measurements; and determining, from said comparison step, hallmarks of said illness of said biological entity, said progression to said death of said biological entity, and/or said death of said biological entity.

BRIEF DESCRIPTION OF THE DRAWINGS

FIG. 1 is a schematic illustration of one embodiment of the present invention.

FIG. 2 illustrates how electrodes may be placed on a hand for the BIA testing procedure.

FIG. 3 illustrates how the electrodes may be placed on the foot for the BIA testing.

DETAILED DESCRIPTION OF THE INVENTION

BIA is an electrodiagnostic methodology based upon the conductive properties of the body's tissues, cells, and fluids. The BIA instrument, such as that disclosed in U.S. Pat. No. 5,372,141, an impedance plethysmograph, may use a constant current source producing a low-voltage electrical signal, usually 800 micro-amps at a high frequency, often fixed at 50 KHz, to set up an electrical field in the whole body or a body segment using a pair of surface ECG-type electrodes.

The methods of the present invention can utilize a modification of the body composition analyzer disclosed in U.S. Pat. 5,372,141, the entire contents of which are incorporated herein by reference thereto.

In accordance with the present invention, utilization of BIA in a biological model for BCA provides an objective assessment of the study subject's (whole body or organ) volume and distribution of fluids and tissues, as well as the electrical health of the cells and membranes.

The characteristics of BIA include precision, accuracy, feasibility and economy. BIA may be applied to any area of interest, regionally or to the whole body. It is non-offensive, causing no harm. It may be repeated freely, as desired, to illustrate change over time so that progression of conditions can be monitored and intervention modified.

One aspect of the present invention applies the BIA technology for BCA assessment of vitality of organs for transplant, vitality of organs from other species for human transplantation (xenotransplantation), and to monitor and assess the timing of death.

Organ vitality assessment is based upon the ability of a modified BIA for BCA to illustrate the health of cells by the measured reactance (X).

Upon organ harvest, signal introduction electrodes are placed on the opposite lateral peripheral borders of the organ being assessed, and signal detection electrodes are placed at the superior and inferior borders of the organ being assessed for the first part of the initial measurement.

The values of electrical resistance (R) and impedance (X) are measured and recorded.

The signal introduction electrodes are then re-positioned or placed on the superior and inferior borders of the organ being assessed, while the signal detection electrodes are now repositioned or placed the opposite lateral peripheral borders of the organ being assessed.

Further values of R and X are measured and recorded.

The values are then compared to normal values, and the organ is determined to be acceptable or not.

If acceptable, prior to organ implant (transplantation or xenotransplantation), the sequence of steps described hereinabove is repeated with comparison being made to the electrical values which were measured and recorded upon organ harvest.

The values should be within an acceptable range of agreement denoting no further loss of organ vitality, and then the implantation is completed.

In accordance with the present invention, the same scenario is utilized for organs from different species.

For determination of the timing of death, whole body measurements are made at predetermined intervals of time (preferably, but not necessarily, every other day) with electrical resistance (R), reactance (X), and phase angle ($\phi$) being measured and recorded. Initial values are compared to normal values and to those serially measured and recorded.

The uncorrectable loss of cell mass and membrane capacity, as evidenced by a reduction in X and $\phi$ or by an uncorrectable and increasing disparity of ECW (extracellular water) volume being greater than ICW (intracellular water) volume and remaining uncorrectable, are the hallmarks of the progression to the death of the biological entity.

$\phi$ values less than four degrees denote serious illness.

$\phi$ values less than two degrees denote imminent demise.

One embodiment of the present invention provides a method for determining illness of a biological entity, progression to death of said biological entity, and/or timing of death of said biological entity, comprising the steps of: taking whole body measurements of resistance, reactance, phase angle, extracellular water volume, and intracellular water volume at predetermined intervals of time; recording said whole body measurements; comparing initial values of said whole body measurements to normal values of said whole body measurements and to serially measured values of said whole body measurements; and determining from said comparison step hallmarks of said illness of said biological entity, said progression to said death of said biological entity, and/or said death of said biological entity.

Another embodiment of the present invention provides a method of organ vitality assessment for transplantation of said organ being assessed, comprising the steps of: placing signal introduction electrodes on opposite lateral peripheral borders of said organ upon harvesting of said organ; placing signal detection electrodes at superior and inferior borders of said organ for a first part of an initial measurement upon said harvesting of said organ; measuring and recording first values of resistance and reactance of said organ in said initial measurement; then placing said signal introduction electrodes on said superior and said inferior borders of said organ; placing said signal detection electrodes on said opposite lateral borders of said organ; measuring and recording second values of said resistance and said reactance of said organ; and comparing said first and second values to normal values to determine if said organ is acceptable or not for said transplantation.

There will now be described a preferred embodiment of the present invention. The preferred embodiment provides a method and apparatus for use in detecting the presence and severity of illness, the effectiveness of treatment interventions, and the ability to change treatment to be more effective or aggressive; to optimize outcome, limit morbidity and mortality and illustrate the patient's prognosis.

The purpose of the preferred embodiment is to empower the healthcare provider and the patient by detecting and characterizing the presence and nature of illness and injury to include episodic, serious, and non-episodic illness and injury, its progression, and the effectiveness of treatment interventions and the prognosis of the patient.

There is provided a method and system for use in detecting the presence and severity of illness in diagnosing and treating a patient to optimize the treatment intervention and determine the prognosis of the patient.

This system employs the use of Whole Body Impedance Analysis to measure the patient's Resistance, Reactance, Phase Angle, and related electrical values at a healthy baseline, and thereafter in relation to the patient's complaints to evaluate the temporal or progressive nature of negative values or diminution of the measured values over time.

Specifically, the system identifies the patient's healthy baseline measured electrical values and, during routine health examinations or when the patient complains of any symptoms or experiences any signs of illness or injury, illustrates excursion from the baseline values that may exceed a thirty-day time frame or progressively diminish. Episodic illness and recoverable injury is characterized by a brief, less than thirty days, excursion below the baseline values and return to the baseline values. More severe illness and injury are characterized by progressive or rapid diminution of the measured values.

Once an effective treatment intervention is begun, the measured values will stabilize and then return to the baseline values indicative of the patient's positive prognosis. More effective treatment is indicated by a more rapid return to baseline-measured values. If the values do not improve, a modified or more aggressive treatment intervention is indicated whose positive effectiveness will be indicated by the initial stabilization of the measured values and their subsequent return to baseline values. Prognosis is proportional to the speed and direction of the return of the measured value to or from the baseline values. A positive prognosis is indicated by a progressive and/or rapid return to the measure baseline values. A negative prognosis is indicated by a progressive and/or rapid diminution of the measured values. The speed of loss or gain of the measured values is proportional to the return of health or the severity of the illness or injury. A neutral or stabilized measured value lower than the healthy baseline, over an extended period of time, greater than six months, indicates a new baseline, a less healthy condition and pre-disposition to future illness.

Frequency of measurements is in proportion to the severity of the process to be illustrated; more severe illness or injury, characterized by more severe symptoms, signs and negative laboratory findings and progressive and/or rapid diminution of the measured values, require more frequent measurements, daily and every other day. Less severe illnesses and injuries may be illustrated with weekly measurements.

The invention will now be further explained with reference to FIGS. 1–3.

The primary study method for an impedance plethysymographic examination either Whole Body 1 or Regional 2 is simple and straightforward. The patient requires no advanced preparation for the study. However, the patient should not be diaphoretic, soaked in urine or any other surface liquid that would provide an alternative pathway for the conduction of the electrical signal that is the basis of the study.

The patient is counseled to lie quietly, motionless, and informed that the test will take less than five minutes if the patent is cooperative. The patient is generally placed in a supine position with arms and legs abducted about thirty degrees from the midline on a dry non-conductive surface. Whole Body 1 and Regional 2 studies require a tetrapolar electrode scheme in which placement of four (two pairs) surface, ECG electrodes in strict relation to anatomical landmarks at the wrist and ankle. If the patient's skin is either too dry or too oily, wiping the electrode placement area with an alcohol prep wipe is suggested. The right side of the body is generally used with the electrodes placed ipsilaterally. However if the patient's condition requires contra-lateral placement and alternative body positions, they can be utilized with the understanding and proviso that the same position will be repeated with all future measurements. The signal detection (SD) electrodes 3 or 4 must be placed with the greatest precision in relation to known anatomical landmarks on both the wrist and the ankle.

On the wrist, the superior linear border of the electrode, its top straight line, must equally bisect the ulnar stylus, bone prominence (bump) on the little finger side of the wrist with the tab of the electrode facing away from the body of the patient. The signal introduction (SI) electrodes 5 are placed distal from the SD electrodes 3 and must be kept at a minimum distance that equals or exceeds that of the diameter of the segment being measured (e.g., the wrist). This is most easily and efficiently accomplished by using the distal phalanx of the middle finger, just proximal to the nail.

On the ankle, the SD electrode 4 is placed so that the superior linear border equally bisects the medial malleolous (the bump on the big toe side of the ankle) with the tab facing outwards from the patient. Care should be exercised to use the medical malleolous because the lateral malleolous (the bump on the little toe side of the ankle) is inferior or below the medial malleolous landmark. The SI electrode 6 is placed on the big toe, as shown in FIG. 1.

The plethysmograph is connected via patient cable leads with strict attention paid to SI and SD leads connected to SI and SD electrodes. The device is energized and the values of resistance and reactance in ohms, are measured individually, allowing a moment (ten to fifteen seconds) to settle, and then are recorded. The electrodes are carefully removed so as not to injure friable skin or contaminate the examiner.

Any standard impedance plethysmograph that utilizes a 500–800 micro-amp constant current electrical source at 50-kilohertz frequency can be utilized. Preferably, but not necessarily, an RJL Systems, Inc. manufactured Quantum II instrument system may be used for both Whole Body 1 and Regional 2 measurements.

For Regional 2 measurements, the patient is prepared in the same manner as with a Whole Body 1 examination. For Regional 2 measurements of the chest, abdomen or extremities (arms/legs, left-right, upper or lower), the signal detection electrodes 7 are placed superiorly and inferiorly in precise relation to the area of interest. The distance between the detection electrodes is precisely measured and recorded in centimeters. The skin is marked with a surgical pen to assure accurate and reproducible electrode placement for serial measurements. The SI electrodes 1 are best placed in the standard Whole-Body locations, however this requires a specialized patient cable with adequate distance or throw, about eighteen inches of length allowed, between the insertion point into the patient cable to and from the clip ends.

The impedance plethysmograph is connected via the patient cables with strict adherence to the SD lead to the SD electrode and the SI lead to the SI electrode. The measured values are recorded and the electrodes carefully removed.

The measured values, resistance, reactance and phase angle are recorded, archived and graphically presented to illustrate change over time and illuminate the processes of disease progression and response to treatment. The frequency of serial measurements is proportional to the dynamic of the event to be captured. If at all possible, a baseline study value is particularly desirable.

Disorders characterized by dynamic shifts of extracellular fluid volumes require more frequent measurements, often prior to and after a procedure or treatment such as a patient requiring hemodialysis, aggressive diuresis in organ failure or repletion of fluids in acute dehydration or trauma. The measured resistance value in ohms is inversely proportional to the extracellular fluid volume of the patient. When resistance ohms decrease fluid has increased and conversely when resistance ohms increase fluid volume has decreased. So, once an initial ohm measurement value is established by baseline or first study, subsequent measurements illustrate the patient's course and response to disease progression and the effectiveness of the selected treatment intervention. The severity of the disease or insult condition evidenced by the speed of the excursion from baseline or initial measurement value. Fluid changes that move more than fifty ohms in a twenty-four hour period are severe and indicate a more acute and serious condition than those that move fifty ohms in a week's time indicative of a more chronic condition. Both conditions require intervention, however as chronic insidious changes are as adverse to survival as more rapid changes. These changes may be evidenced in both Whole Body 1 and Regional 2 measurements. Whole Body 1 measurements are more general in their value, indicative of conditions and events that encompass the organism as a whole such as cardiac or renal failure and acute dehydration. Regional 2 measurements provide a site-specific assessment of fluid volumes such as those found with pleural effusion in the chest, ascites in the abdomen or even cerebral edema. The changes of measured electrical values precede changes seen on x-ray, physical examination, or from laboratory studies.

Once again, increasing ohms of resistance indicate a drying and fluid reduction while decreasing ohms of resistance indicate increased fluid volumes. Thoracic resistance values that are increasing indicate a drying chest and conversely decreasing resistance values indicate additional accumulation of fluid. These changes clearly indicate the improvement or worsening of disease conditions and the individual's response to treatment and ergo, its effectiveness. The extent and aggressiveness of therapy can be altered and modified to "optimize" the beneficial effects.

Reactance values are proportional to the number and integrity (health) of cell wall membranes so when cells increase or decrease reactance values follow. The cells that change in this manner are those of the somatic and visceral protein tissues, such as skeletal musculature organs such as the liver, spleen, lungs, heart stomach and intestines. Cellular alterations are generally slower to occur and are affected by metabolic and specific disease processes. However, overly aggressive diuresis, excessive hemodialysis or cellular targeted pathologies such as Rhabdomyolysis can all result in rapid, days versus a week, changes in cell mass, membrane status and measured reactance values. Excursions from the baseline or initial measurement value indicate the type and progression of disease and/or the effectiveness of treatment interventions. Increased cells (membranes) and anabolic metabolism are evidenced by a rise in the ohms of reactance, generally a sign of improvement. A slowly decreasing ohm value of reactance indicates a negative or catabolic metabolism condition. A more precipitous and rapid decrease in reactance is indicative of unique conditions that rapidly affect cells and their membranes, such as the effect of Rhabdomyolysis skeletal muscle or rejection or infection of an organ system.

Regional measurement values of ohms of reactance are used for these disease specific investigations while whole body values are used for the assessment of metabolic evaluation.

A derivative of the measured values of resistance and reactance is the arc tangent of reactance to resistance expressed in degrees or Phase Angle. Phase Angle is the cumulative expression of the changes and ratios of cell mass and extracellular fluid that result from disease, insult and/or treatment intervention and can by itself be used to gauge the severity and progression of pathologies and the effectiveness and benefits of treatment. A positive prognosis is indicated by an increasing phase angle while a poor prognosis is associated with a phase angle decrease. Phase angle has been correlated with survival and the timing of non-acute death. Phase angle can be derived from both whole body and regional measurements and followed serially to establish prognosis.

Treatment interventions can be measured for their effectiveness on the individual patient by following phase angle. More effective treatments are evidenced by an increasing phase angle while those less effective are seen as producing little or no increase. Once phase angle degrades to below four degrees, the patient is seriously ill and treatment should be aggressive and modified to be effective and optimal. If phase angle does not stabilize or increase through multiple iterations of treatment, a curative or restorative treatment goal outcome is doubtful. A phase angle of less than two degrees is associated with pending mortality and a need for palliative care and comfort. Admission to a hospice can be objectively based upon phase angle monitoring providing the patient with improved end-of-life care and comfort.

FIG. 2 illustrates how electrodes may be placed on the hand for the BIA Testing Procedure.

The detecting electrode edge 8 is placed on an imaginary line bisecting the ulna head (bone on little finger side of wrist)

The signal electrode 9 is placed on the first joint of the middle finger.

FIG. 3 illustrates how electrodes may be placed on the foot.

The detecting electrode edge 10 is placed on an imaginary line bisecting the medial mellealus (bone on big toe side of ankle).

The signal electrode 11 is placed on the base of the second toe.

The exam area should be comfortable and free of drafts and portable electric heaters. The exam table surface must be non-conductive and large enough for the subject to line supine with the arms 30 degrees from the body, and legs not in contact with each other.

The subject should not have exercised or taken a sauna within 18 hours of the study. The subject should refrain from alcohol intake for 12 hours prior to the study. The subject's height and weight should be accurately measured and recorded. The subject should lie quietly during the entire test. The subject should not be wet from sweat or urine. The subject should not have a fever or be in shock. The study and testing procedure should be explained to the subject.

The subject should remove the shoe and sock and any jewelry on the electrode side (generally the study is completed on the right side of the body). The body side (left or right) should always be used subsequently.

The subject should lie supine with the arms 30 degrees from the body with legs not touching.

The electrode sites may be cleaned with alcohol, particularly if the skin is dry or covered with lotion.

The electrodes and patient cables are attached as shown in FIGS. 2 and 3.

The analyzer is turned on, making sure the subject refrains from moving. When the measurements have stabilized, record the displayed Resistance (R) and Reactance (Xc) with the subject's name, age, gender, height and weight.

The entire testing time is less than 5 minutes—the BIA analyzer is on for less than one minute.

The results are available immediately from the software program.

The study may be repeated as often as necessary.

The present invention also embraces the features of using the invention for various areas of interest, for example, whole-body thoracic, abdominal, extremity, etc.

Although the invention has been described in detail in the foregoing only for the purpose of illustration, it is to be understood that such detail is solely for that purpose and that variations and modifications can be made therein by those of ordinary skill in the art without departing from the spirit and scope of the invention including all equivalents thereof.

What is claimed is:

1. A method for detecting the presence and severity of illness, the effectiveness of treatment interventions, and the ability to change treatment to be more effective or aggressive, to optimize outcome, limit morbidity and mortality and illustrate the patient's prognosis, comprising the steps of:
    employing the use of whole body impedance analysis to measure a patient's resistance, reactance, phase angle, and related electrical values at a healthy baseline; and
    thereafter in relation to the patient's complaints, evaluating temporal or progressive nature of negative values or diminution of said measured values of said patient's resistance, reactance, phase angle, and related electrical values over time.

2. A method according to claim 1, including:
    identifying the patient's healthy baseline electrical values; and
    during routine health examinations or when the patient complains of any symptoms or experiences any signs of illness or injury, illustrating excursion from said baseline values which exceed a thirty-day timeline or progressively diminish.

3. A method according to claim 1, wherein:
    values of said phase angle less than four degrees denote serious illness of the patient; and
    values of said phase angle less than two degrees denote imminent death of the patient.

4. A method according to claim 2, wherein:
    values of said phase angle less than four degrees denote serious illness of the patient; and
    values of said phase angle less than two degrees denote imminent death of the patient.

5. A method for detecting the presence and severity of illness, the effectiveness of treatment interventions, and the ability to change treatment to be more effective or aggressive, to optimize outcomes, to limit morbidity and mortality and illustrate the prognosis for a patient, comprising the steps of:
    employing whole body impedance analysis to take a first measurement of resistance, reactance, phase angle, and related electrical values of a patient at a healthy baseline;
    thereafter in relation to complaints of said patient, again employing whole body impedance analysis to take a second measurement of said resistance, reactance, phase angle and related electrical values of said patient; and
    evaluating temporal or progressive nature of negative values of diminution of said measured values of resistance, reactance, phase angle, and related electrical values over time.

6. A method according to claim 5, including:
    identifying the patient's healthy baseline electrical values; and
    during routine health examinations or when the patient complains of any symptoms or experiences any signs of illness or injury, illustrating excursion from said baseline values which exceed a thirty-day timeline or progressively diminish.

7. A method according to claim 5, wherein:
    values of said phase angle less than four degrees denote serious illness of the patient; and
    values of said phase angle less than two degrees denote imminent death of the patient.

8. A method according to claim 6, wherein:
    values of said phase angle less than four degrees denote serious illness of the patient; and
    values of said phase angle less than two degrees denote imminent death of the patient.

9. A method according to claim 5, including the steps of:
    recording, archiving, and graphically presenting said measured values of resistance, reactance, phase angle and related electrical values to illustrate changes over time and to illuminate processes of disease progression and response to treatment.

10. A method according to claim 6, including the steps of:
    recording, archiving, and graphically presenting said measured values of resistance, reactance, phase angle and related electrical values to illustrate changes over time and to illuminate processes of disease progression and response to treatment.

11. A method according to claim 7, including the steps of:
    recording, archiving, and graphically presenting said measured values of resistance, reactance, phase angle and related electrical values to illustrate changes over time and to illuminate processes of disease progression and response to treatment.

12. A method according to claim 8, including the steps of:
    recording, archiving, and graphically presenting said measured values of resistance, reactance, phase angle and related electrical values to illustrate changes over time and to illuminate processes of disease progression and response to treatment.

13. A method according to claim 5, wherein:
    episodic illness and recoverable injury is characterized by a less than 30-day excursion below said baseline values and return to said baseline values.

14. A method according to claim 6, wherein:
    episodic illness and recoverable injury is characterized by a less than 30-day excursion below said baseline values and return to said baseline values.

15. A method according to claim 7, wherein:

episodic illness and recoverable injury is characterized by a less than 30-day excursion below said baseline values and return to said baseline values.

16. A method according to claim 8, wherein:

episodic illness and recoverable injury is characterized by a less than 30-day excursion below said baseline values and return to said baseline values.

17. A method according to claim 9, wherein:

episodic illness and recoverable injury is characterized by a less than 30-day excursion below said baseline values and return to said baseline values.

18. A method according to claim 10, wherein:

episodic illness and recoverable injury is characterized by a less than 30-day excursion below said baseline values and return to said baseline values.

19. A method according to claim 11, wherein:

episodic illness and recoverable injury is characterized by a less than 30-day excursion below said baseline values and return to said baseline values.

20. A method according to claim 12, wherein:

episodic illness and recoverable injury is characterized by a less than 30-day excursion below said baseline values and return to said baseline values.

\* \* \* \* \*